United States Patent
Ling et al.

(10) Patent No.: US 11,740,167 B2
(45) Date of Patent: Aug. 29, 2023

(54) TEMPERATURE-CONTROLLABLE LARGE-SIZE GEOTECHNIQUE TRUE TRIAXIAL MULTI-FIELD COUPLING TEST SYSTEM AND TEST METHOD

(71) Applicant: QINGDAO UNIVERSITY OF TECHNOLOGY, Qingdao (CN)

(72) Inventors: Xianzhang Ling, Qingdao (CN); Lei Su, Qingdao (CN); Yingying Zhao, Qingdao (CN); Liang Tang, Qingdao (CN); Ruxiang Zhao, Qingdao (CN)

(73) Assignee: Qingdao University of Technology, Qingdao (CN)

( * ) Notice: Subject to any disclaimer, the term of this patent is extended or adjusted under 35 U.S.C. 154(b) by 160 days.

(21) Appl. No.: 17/435,959

(22) PCT Filed: Jun. 22, 2020

(86) PCT No.: PCT/CN2020/097457
§ 371 (c)(1),
(2) Date: Sep. 2, 2021

(87) PCT Pub. No.: WO2021/098206
PCT Pub. Date: May 27, 2021

(65) Prior Publication Data
US 2022/0146387 A1 May 12, 2022

(30) Foreign Application Priority Data
Nov. 21, 2019 (CN) .......................... 201911150561.9

(51) Int. Cl.
*G01N 3/18* (2006.01)
*G01N 3/12* (2006.01)
(Continued)

(52) U.S. Cl.
CPC ................. *G01N 3/18* (2013.01); *G01N 3/12* (2013.01); *G01N 23/20* (2013.01); *G01N 29/04* (2013.01); *G01N 33/24* (2013.01)

(58) Field of Classification Search
CPC ............ G01N 3/18; G01N 3/12; G01N 23/20; G01N 29/04; G01N 33/24
(Continued)

(56) References Cited

FOREIGN PATENT DOCUMENTS

| CN | 108645885 A | * | 10/2018 | ............. G01N 25/00 |
|---|---|---|---|---|
| CN | 110132719 A | * | 8/2019 | |

OTHER PUBLICATIONS

Translation of Su et al., CN-110132719-A (Year: 2019).*
Translation of Wei et al., CN-108645885-A (Year: 2018).*

* cited by examiner

*Primary Examiner* — Nathaniel T Woodward
(74) *Attorney, Agent, or Firm* — Katten Muchin Rosenman LLP

(57) ABSTRACT

The present disclosure discloses a temperature-controllable large-size geotechnique true triaxial multi-field coupling test system and a test method. The system includes a host loading mechanism, a deformable large-size soil box, an independent three-dimensional loading unit, a refrigeration, water and salt supplementation unit, and a soil-water-ice-salt change monitoring unit. The deformable large-size soil box is arranged on the host loading mechanism. In combination with the special structural design, monitoring is carried out by dividing a large-size soil test sample into environmental soil and a core soil region to eliminate the size effect of the test. The solution can simulate a three-dimensional stress state of the soil test sample in a three-dimensional open system. In consideration of the evolution of hydrothermal salt and three-dimensional migration of temperature, water, (Continued)

salt, etc. between the soil and the environment, temperature-water-salt-stress-strain multi-field coupling is realized.

10 Claims, 14 Drawing Sheets

(51) Int. Cl.
*G01N 23/20* (2018.01)
*G01N 29/04* (2006.01)
*G01N 33/24* (2006.01)

(58) Field of Classification Search
USPC .......................................................... 73/796
See application file for complete search history.

TEMPERATURE-CONTROLLABLE LARGE-SIZE GEOTECHNIQUE TRUE TRIAXIAL MULTI-FIELD COUPLING TEST SYSTEM AND TEST METHOD

CROSS REFERENCE TO RELATED APPLICATIONS

This patent application is 35 U.S.C. § 371 national stage application of PCT/CN2020/097457 filed Jun. 22, 2020 which claims the benefit and priority of Chinese Patent Application No. 201911150561.9, filed on Nov. 21, 2019, the disclosure of which is incorporated by reference herein in its entirety as part of the present application.

TECHNICAL FIELD

The present disclosure belongs to the technical field of geotechnique true triaxial tests, and specifically relates to a temperature-controllable large-size geotechnique true triaxial multi-field coupling test system and a test method.

BACKGROUND

Conventional geotechnical triaxial test system is essentially in an axisymmetric stress state, which cannot truly reflect the complex stress conditions experienced by the actual soil. Only the strength parameters of the soil in the axisymmetric stress state are measured. In order to better and truly simulate an actual stress state of the soil, analyze the stress, strain and strength characteristics of the soil in a three-dimensional spatial under the condition of independent changes of three principal stresses, a true triaxial test system is researched and developed.

The true triaxial test system is divided into three forms: rigid, flexible, and composite according to loading characteristics of a pressure chamber, is divided into full rigidity of strain control, full flexibility of stress control, rigidity and flexibility of composite control according to a load method, is divided into a three-directional rigid plate, a bidirectional rigid plate and a unidirectional flexible hydraulic bag or fluid confining pressure, a three-directional flexible hydraulic bag, etc. However, soil test samples of the existing true triaxial test device are all completely packaged or are closed at the peripheries, so that the open state of the actual soil cannot be simulated. There is no way to achieve the actual temperature, water, salt, and other three-dimensional migration processes between the soil test samples and the environment. For example, in a multi-field coupling true triaxial test system and a test method thereof which are disclosed in the invention patent application No. CN 107576562 A, by controlling a stress field and a seepage field, the anisotropism of seepage in the rock-soil body can be simulated and studied, and the physical and mechanical properties of unsaturated soil under a multi-field coupling condition can be simulated and studied. In addition, smaller test samples are often used in the traditional true triaxial test system, and are essentially in a point test. It is impossible to set more sensors (too many sensors have greater impact on the performance of test pieces) due to the smaller test pieces. The test pieces have a relatively large-scale effect problem. That is, the smaller the test piece is, the greater the impact of the scale on a test result. It is difficult to solve the practical problem of the multi-field coupling effect.

At present, there is no multi-functional test equipment that integrates temperature control, large size and multi-field coupling (in practice, most of them are ordinary/temperature-controllable triaxial test systems or small-size temperature-controllable true triaxial test systems). It is impossible to realize the combined dynamic and static experimental studies of the multi-field coupling effects such as the temperature, the water, the salt, the stress and the strain in engineering geological environments in cold regions. In view of this, it is urgent to propose a temperature-controllable large-size geotechnical true triaxial multi-field coupling test system to fully consider the evolution and migration of hydrothermal salt and realize the multi-field coupling effect of temperature-water-salt-stress-strain. The problem of three-dimensional migration of temperature, water and salt between the soil and the environment is solved, and an actual three-dimensional open system and a real three-dimensional stress state are simulated.

SUMMARY

For the deficiencies of an existing multi-field coupling test system, the present disclosure provides a temperature-controllable large-size geotechnical true triaxial multi-field coupling test system and a test method. The system shows the characteristics of simple structure, easy machining and convenience of operation. A stress state of actual soil is better simulated. The whole true triaxial test system is relatively high in safety, reliability and economy.

The present disclosure is realized by the following technical solutions. A temperature-controllable large-size geotechnical true triaxial multi-field coupling test system includes a host loading mechanism, a deformable large-size soil box, an independent three-dimensional loading unit, a refrigeration, water and salt supplementation unit, and a soil-water-ice-salt change monitoring unit. The deformable large-size soil box is arranged on the host loading mechanism; the independent three-dimensional loading unit, the refrigeration, water and salt supplementation unit, and the soil-water-ice-salt change monitoring unit are all connected with the deformable large-size soil box to respectively correspondingly apply stress to the soil box, supplement refrigeration as well as water and salt, and monitor soil-water-ice-salt changes.

The host loading mechanism includes a carrier base, a vertical loading framework, and a horizontal loading framework; the carrier base includes a carrier table located below the vertical loading framework and a rail seat extending in a horizontal direction of the carrier table; the horizontal loading framework includes a workbench, a lateral reaction frame, and a moving lifting wheel disposed below the workbench; the lateral reaction frame is disposed on the workbench through a lateral pressure vertical column; and the deformable large-size soil box is disposed on the workbench and is surrounded by the lateral reaction frame.

The deformable large-size soil box includes a bottom plate, soil box side plates, a soil box horizontal deformation limiting device and a normal loading plate; a water supply and drainage trough is arranged on the bottom plate; a water permeation plate is arranged on the water supply and drainage trough; a lateral sliding device is also arranged on the outer side of the soil box side plates; a lateral oil cylinder is fixedly provided on the lateral reaction frame; the lateral oil cylinder passes through the lateral reaction frame and is connected with the lateral sliding device; and the lateral oil cylinder slides along the lateral sliding device in the deformation process of the deformable large-size soil box.

Further, the refrigeration, water and salt supplementation unit includes a refrigeration module and a water and salt supplementation module; the refrigeration module includes a cooling pipe arranged below a groove on the inner lower side of the normal loading plate and the water permeation plate, and refrigeration equipment connected with the cooling pipe; the water and salt supplementation module is connected with the water supply and drainage trough on the bottom plate through a circulating pipe, and is used to convey water or salt to the bottom plate through the circulating plate; and the water or salt is permeated from the water supply and drainage trough to the water permeation plate to supplement water or salt to the soil under the capillary action.

Further, the soil-water-ice-salt change monitoring unit includes a soil structure change monitoring module and a water-ice-salt change monitoring module; the soil structure change monitoring module includes an ultrasonic device, an ultrasonic stimulation probe and a receiving probe; the ultrasonic stimulation probe and the receiving probe are correspondingly arranged on the outer side of the deformable large-size soil box respectively; the water-ice-salt change monitoring module includes monitoring sensors arranged at different depths in an environmental soil region to monitor the water, ice, and salt contents of the soil.

Further, the soil in the deformable large-size soil box is divided into a core soil region and the environmental soil region surrounding the core soil region; the monitoring sensors include a plurality of neutron scatterometers arranged vertically in the environmental soil at intervals from top to bottom; and a TDR probe is arranged within a radiation radius of each neutron scatterometer.

Further, the core soil region is of a core column structure with length 1.0 m×width 1.0 m×height 1.0 m; and the environmental soil region is of a ring column structure obtained by removing the core soil region from a cubic structure with length 1.2 m×width 1.2 m×height 1.0 m.

Further, the independent three-dimensional loading unit includes a horizontal power loading module and a normal power loading module; the horizontal power loading module includes a horizontal dowel bar, a level gauge, and a horizontal power loading fine adjustment device; the level gauge is arranged on the horizontal dowel bar; the normal power loading module includes a normal power loading device, a hollow square fender, and a cross beam; an axial force is applied to the normal loading plate; and the normal loading plate is downwards transmitted the load to the soil in the soil box.

Further, a push-pull arm is also arranged between the carrier table and the workbench; one end of the push-pull arm is fixedly connected with the workbench, and the other end of the push-pull arm is mounted on the carrier table through a push-pull oil cylinder; and the workbench slides along the rail seat under the action of the push-pull oil cylinder.

Further, the soil box side plates of the deformable large-size soil box include, from outside to inside in sequence, an outer side plate, a thermal insulation plate, and an inner side plate.

Further, grooves are formed in upper and lower surfaces of the water permeation plate; a water-salt pipe is arranged in the upper groove of the water permeation plate; and a cooling pipe is arranged in the lower groove of the water permeation plate.

The present disclosure further provides a test method based on the temperature-controllable large-size geotechnique true triaxial multi-field coupling test system. The test method includes the following steps:

at step 1: pulling out the workbench, and assembling the deformable large-size soil box:

installing the base, the bottom plate, the water supply and drainage trough, and the water permeation plate in sequence, disposing the water supply and drainage trough on the upper surface of the bottom plate, disposing the water permeation plate on the upper surface of the water supply and drainage trough, installing the soil box side plates, completing the assembling of the soil box according to the soil box horizontal deformation limiting device, and disposing waterproof sealing strips between the soil box side plates as well as between the soil box side plates and the bottom plate;

at step 2: filling the soil box with soil layer by layer, arranging the sensors in the environmental soil region, and completing filling of soil test samples:

filling the soil box with the soil layer by layer, arranging the sensors in the environmental soil region, completing the filling of the soil test samples, setting and connecting the water-ice-salt change monitoring module, arranging the corresponding monitoring sensors in the environmental soil region to monitor the water, ice and salt contents of the soil, arranging the soil structure change monitoring module around the soil box side plates, installing the stimulation probe on one side of the soil box, installing the receiving probe on the other side, and reflecting changes of the soil structure in a testing process by means of collecting received signals;

at step 3: resetting the workbench to the carrier table, arranging the hollow square fender, and arranging the normal loading plate in the hollow square fender;

at step 4: connecting the refrigeration, water and salt, connecting the refrigeration equipment to the cooling pipe in the normal loading plate through the circulating pipe to realize apply a temperature load to the top of the soil test sample, and arranging the water and salt supplementation module at the bottom of the bottom plate to apply water and salt to the bottom of the soil; and at step 5: arranging the horizontal power loading module and the normal power loading module to load three stresses in unequal directions.

Compared with the prior art, the present disclosure has the following advantages and beneficial effects.

For a large-size soil test sample, the temperature-controllable multi-field coupling test system of this solution uses a brand-new structural design and can simulate the migration law of the water and the salt of the large-size soil test sample in an open system, and a freezing process and a capillary action process of the actual soil test sample. It is ensured that the core soil region is not affected by the arrangement of the sensors by the ultrasonic monitoring equipment arranged on the outer side of the soil box and the sensors arranged in the environmental soil region. An actual stress state of the soil test sample under the temperature-water-salt-stress-strain multi-field coupling action is reasonably simulated, so that a multi-field coupling system design showing multifunctionality, controllability, simple structure, and machinability is realized, and the actual problem of the multi-field coupling effect can be solved. The technical problems in the study of the multi-field coupling action and the mutual feedback effect in the three-dimensional open system under the three-dimensional stress state of the engineering geological environment in cold regions are solved. Good experimental support conditions are created for further study on the prevention and control of frost damage and disaster control.

DETAILED DESCRIPTION

Figure 1:
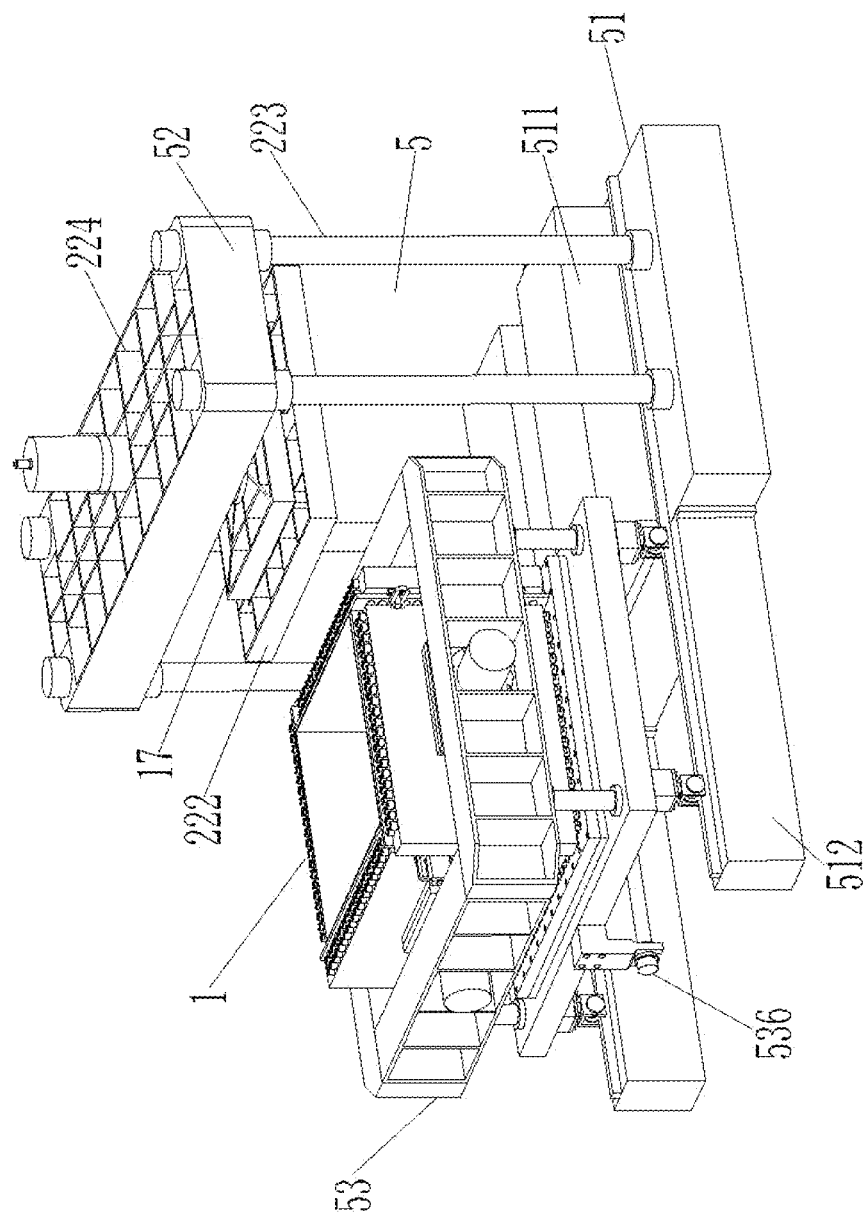
FIG. 1 is a schematic structural diagram of a host loading mechanism and a deformable large-size soil box according to Embodiment 1 of the present disclosure.

In order to understood the above-mentioned objectives and advantages of the invention more clearly, the specific implementation modes of the invention are described in detail below in combination with the accompanying drawings:

Embodiment 1, a temperature-controllable large-size geotechnical true triaxial multi-field coupling test system includes a host loading mechanism 5, a deformable large-size soil box 1, an independent three-dimensional loading unit, a refrigeration, water and salt supplementation unit, and a soil-water-ice-salt change monitoring unit. As shown in FIG. 1, the deformable large-size soil box 1 is arranged on the host loading mechanism 5; the independent three-dimensional loading unit, the refrigeration, water and salt supplementation unit, and the soil-water-ice-salt change monitoring unit are all connected with the deformable large-size soil box to respectively correspondingly apply stress to the soil box, supplement refrigeration as well as water and salt, and monitor soil-water-ice-salt changes.

Figure 11:
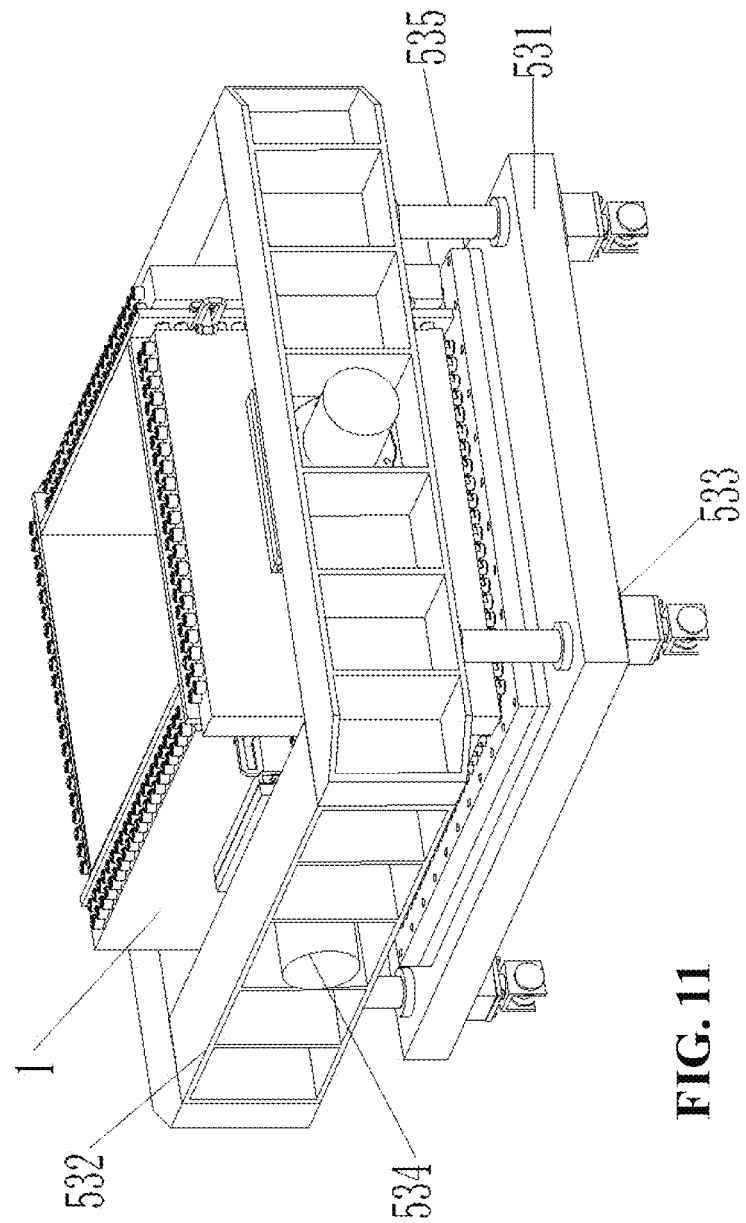
FIG. 11 is a schematic structural diagram of a deformable large-size soil box and a horizontal loading framework according to Embodiment 1 of the present disclosure.
Figure 12:
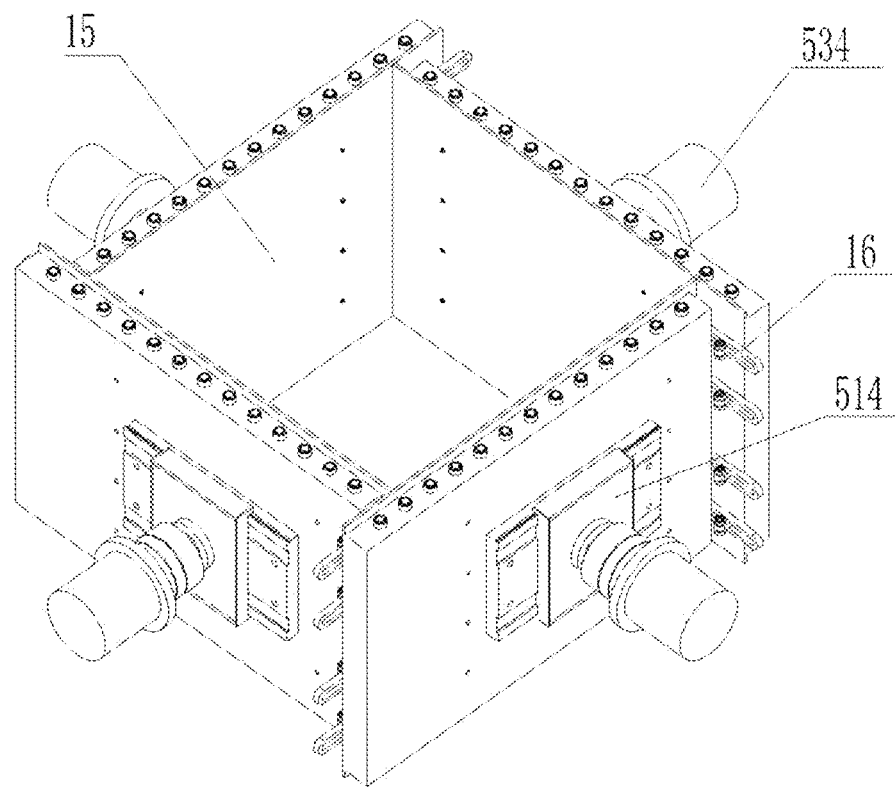
FIG. 12 is a schematic structural diagram of a deformable large-size soil box according to Embodiment 1 of the present disclosure.

Referring to FIG. 1, the host loading mechanism 5 includes a carrier base 51, a vertical loading framework 52, and a horizontal loading framework 53; the carrier base 51 is connected with the vertical loading framework 52 through system vertical columns 223; the carrier base 51 includes a carrier table 511 located below the vertical loading framework 52 and a rail seat 512 extending in a horizontal direction; the horizontal loading framework 53 includes a workbench 531, a lateral reaction frame 532, and a moving lifting wheel 533; four side surfaces of the lateral reaction frame 532 are correspondingly provided with lateral oil cylinders 534 respectively; the lateral reaction frame 532 is provided on the workbench 531 through a lateral pressure vertical column 535; the moving lifting wheel 533 is fixedly arranged below the workbench 531, and can slide along the rail seat 512. As shown in FIG. 11 and FIG. 12, the deformable large-size soil box 1 is provided on the workbench 531 and is surrounded by the lateral reaction frame 532; a lateral sliding device 514 is also arranged on the outer side of the side plates of the deformable large-size soil box 1; the lateral oil cylinders 534 are fixedly arranged on the lateral reaction frame 532, pass through the lateral reaction frame 532, and are connected with the lateral sliding device 514; the lateral oil cylinders 534 may slide left and right along the lateral sliding device 514, so that when a lateral load is applied in the deformation process of the deformable large-size soil box 1, and the size of the soil box changes under a three-directional load, the triaxial principal stresses correspond at the axis in the loading process in combination with cooperation of the lateral oil cylinders, the lateral reaction frame, and the lateral sliding device by means of real-time servo control; coaxial loading is realized; and eccentric loading is avoided.

Figure 13:
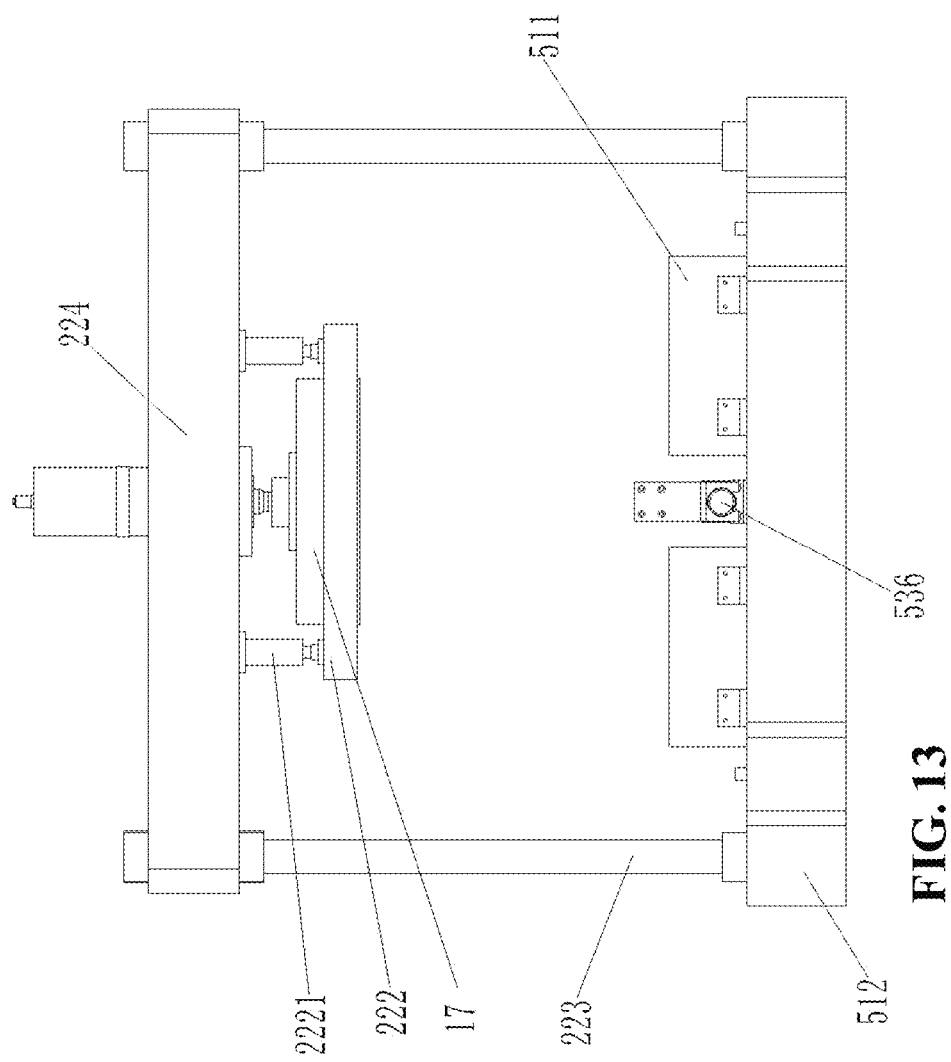
FIG. 13 is a schematic structural diagram I of a host loading framework according to Embodiment 1 of the present invention.
Figure 14:
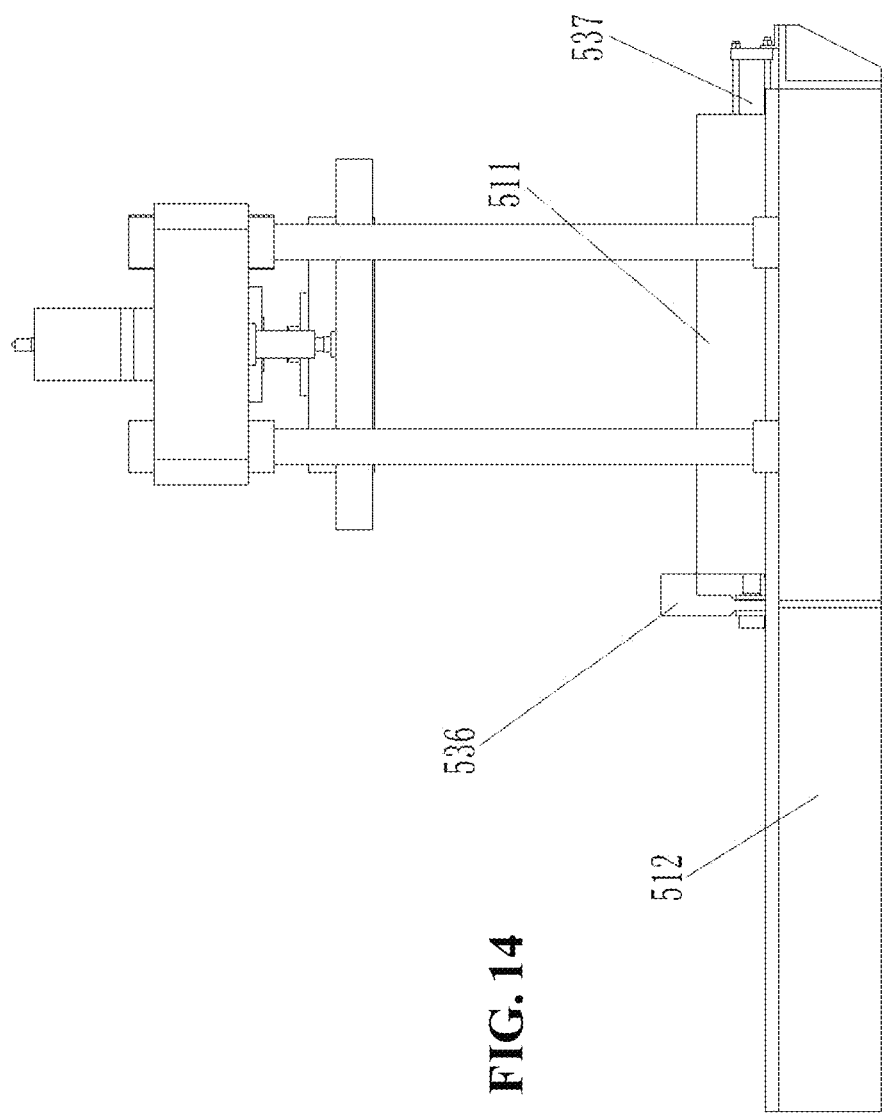
FIG. 14 is a schematic structural diagram II of a host loading framework according to Embodiment 1 of the present invention.

In addition, as shown in FIG. 13 and FIG. 14, a push-pull arm 536 is also arranged between the carrier table 511 and the workbench 531; one end of the push-pull arm 536 is fixedly connected with the workbench 531, and the other end of the push-pull arm is mounted on the carrier table 511 through a push-pull oil cylinder 537; and the workbench 531 horizontally slides along the rail seat 512 under the action of the push-pull oil cylinder 537. During sliding out, the moving lifting wheel 533 is lifted up, so that samples are conveniently put into the large-size soil box; after sliding in, the moving lifting wheel 533 is lowered, a vertical load is directly carried by the carrier table 511, and the moving lifting wheel 533 is not stressed anymore; and related system modules are connected to do the test, so that the operation is more convenient.

Figure 2:
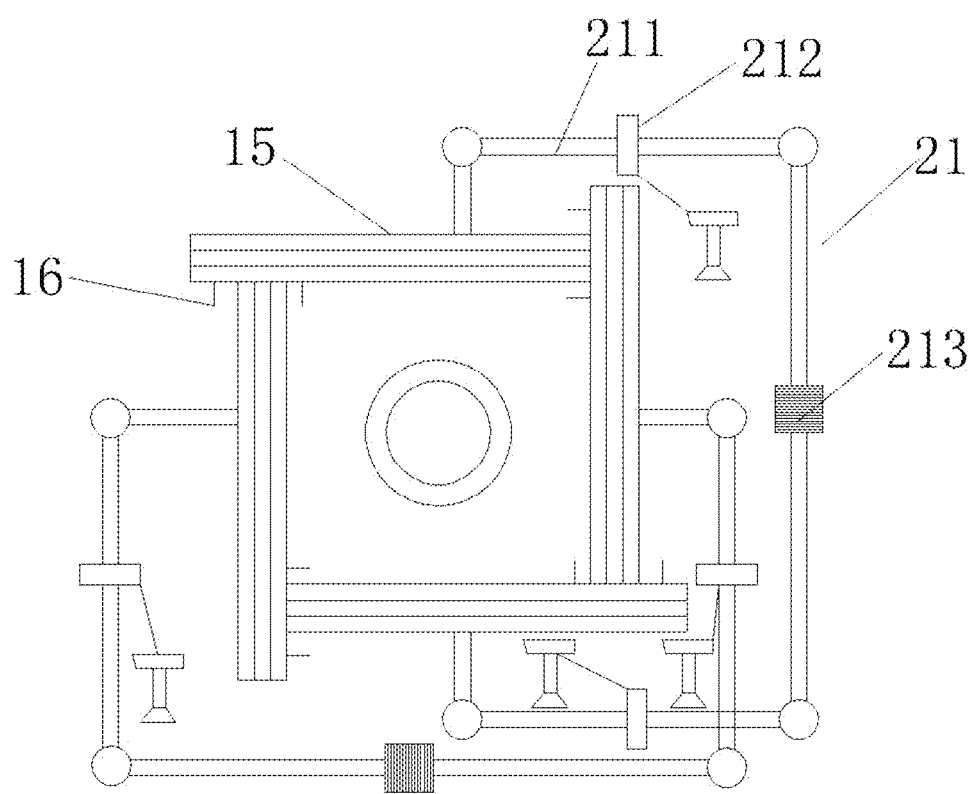
FIG. 2 is a schematic structural diagram of a horizontal power loading module and a deformable large-size soil box according to Embodiment 1 of the present disclosure.
Figure 3:
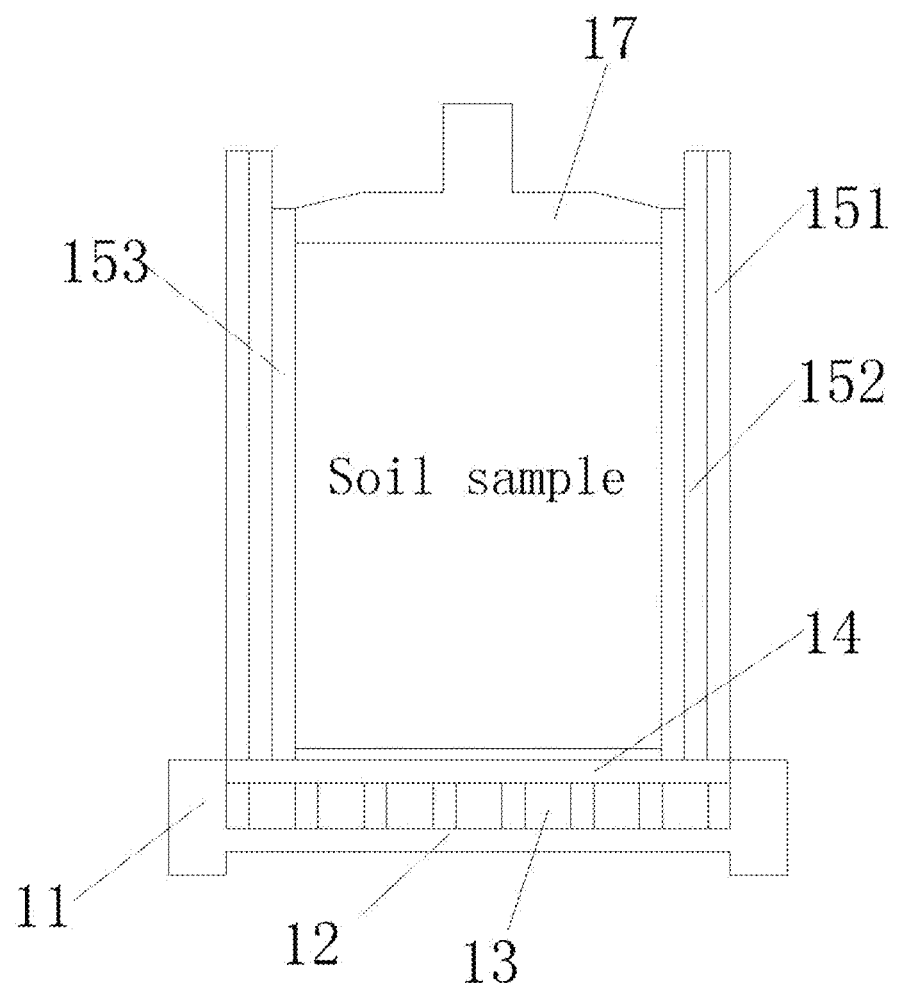
FIG. 3 is a schematic structural diagram of a lateral section of the deformable large-size soil box in Embodiment 1 of the present disclosure.

In the present embodiment, the structural design and a specific sealing design solution of the deformable large-size soil box can be implemented according to the solutions disclosed in the application No. CN 110132719 A and the application No. CN 109752254 A. Of course, other implementable structures may also be used. As shown in FIG. 2 and FIG. 3, the deformable large-size soil box 1 includes a base 11, a bottom plate 12, a water supply and drainage trough 13, a water permeation plate 14, soil box side plates 15, soil box horizontal deformation limiting devices 16 and a normal loading plate 17; the bottom plate 12 is placed on the base 11; the water supply and drainage trough 13 is arranged on the upper surface of the bottom plate 12; a water supply and drainage port is formed in the middle of the bottom plate 12; a cooling pipe groove is formed in the lower side surface of the normal loading plate 17; the water permeation plate 14 is arranged on the upper surface of the water supply and drainage trough 13; the soil box side plates 15 are composed of an outer side plate 151, a thermal insulation plate 152, and an inner side plate 153; the thermal insulation plate is sandwiched between the inner and outer side plates; each soil box horizontal deformation limiting device 16 is mounted on each side plate 15; and the maximum stroke of the side plate 15 depends on the maximum range of the limiting device 16.

Figure 4:
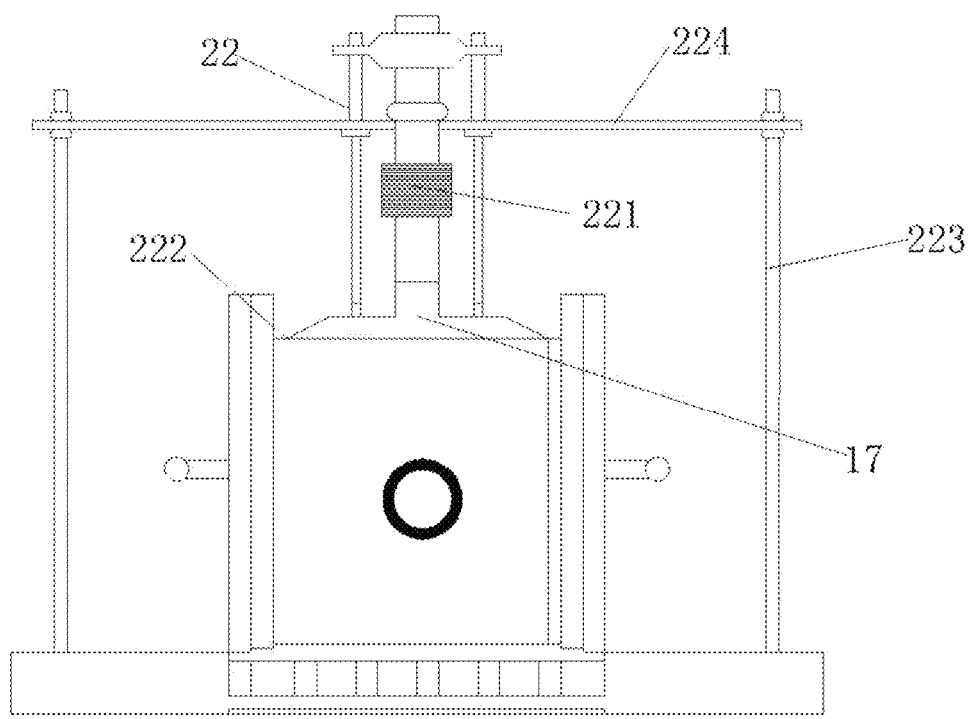
FIG. 4 is a schematic structural diagram of a normal power loading module and a deformable large-size soil box according to Embodiment 1 of the present disclosure.
Figure 5:
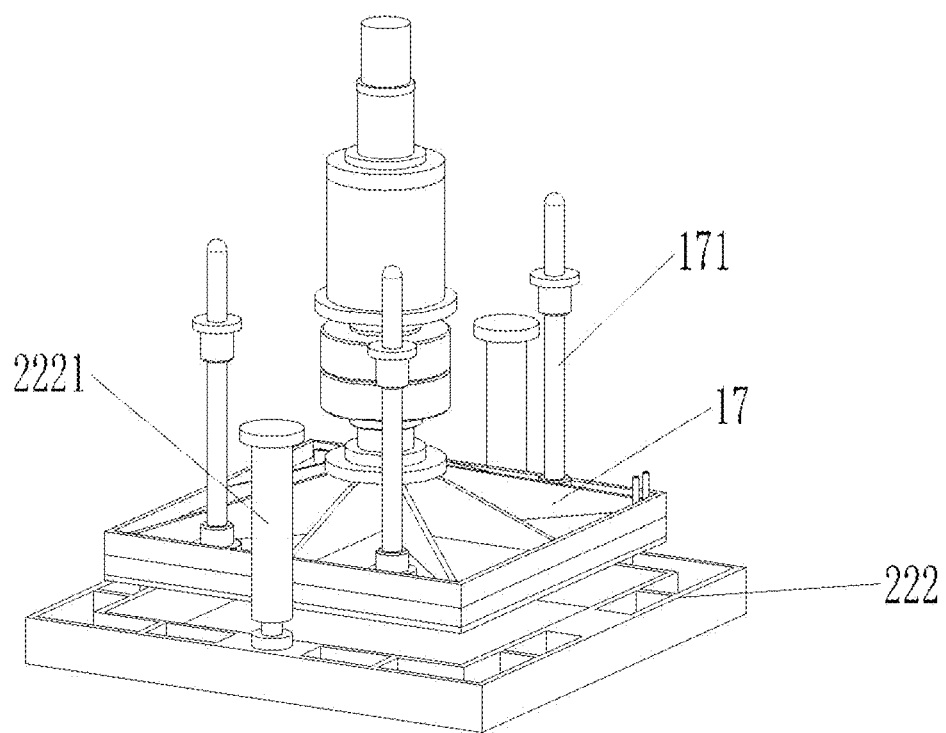
FIG. 5 is a schematic structural diagram of the normal loading plate according to Embodiment 1 of the present invention.

The independent three-dimensional loading unit includes a horizontal power loading module 21 and a normal power loading module 22. Three principal stresses are used to independently control a loading mode, so as to well simulate three stress states (i.e., $\sigma_1 > \sigma_2 = \sigma_3$, $\sigma_1 > \sigma_2 > \sigma_3$, and $K_0$ states). As shown in FIG. 2 and FIG. 4, the schematic diagram is illustrated. The horizontal power loading module 21 includes a horizontal dowel bar 211, a level gauge 212, and a horizontal power loading fine adjustment device 213. A static load, a simple harmonic vibration load, and a random vibration load can be respectively applied according to test needs. The level gauge 212 is provided on the horizontal dowel bar 211. The level gauge 212 is provided to ensure horizontal loading. Equal horizontal loads are ensured to be simultaneously horizontally transmitted to two opposite soil box side plates by using the horizontal dowel bar through the horizontal power loading fine adjustment device 213, and the horizontal dowel bar is in spherical hinge to ensure the center is always stressed in the test. The normal power loading module 22 includes a normal power loading device 221, a hollow square fender 222, system vertical columns 223, and a cross beam 224. An axial force is applied to the normal loading plate 17, and the normal loading plate 17 downwards transmits the load to the soil in the soil box; a maximum axial displacement of the normal loading plate 17 is a thickness of the hollow square fender 222. The hollow square fender 222 is placed at the tops of the side plates. When the side plates 15 move, the hollow square fender 222 is in close contact with the side plates 15. As shown in FIG. 5, a guide device 171 is also arranged on the normal loading plate 17. When the guide device 171 moves up and down under the action of the normal power loading device 221, torsion of the normal loading plate 17 when the normal power loading device applies a load is effectively avoided, a uniformly distributed load is ensured to be applied, and the test is ensured to be reliably carried out. The hollow square fender 222 is located at a peripheral edge of the normal loading plate, and a hollow square fender loading device 2221 is also arranged above the hollow square fender 222 to ensure that the hollow square fender is not twisted in the testing process. Meanwhile, the hollow square fender is in tight connection with the soil box side plates to ensure that the soil in the soil box does not come out in the loading process. When there is soil coming out, the hollow square fender loading device 2221 applies a certain resistance, and the normal loading plate passes though the hollow square fender and applies a normal load to the soil in the soil box under the action of the normal power loading device.

Figure 6:
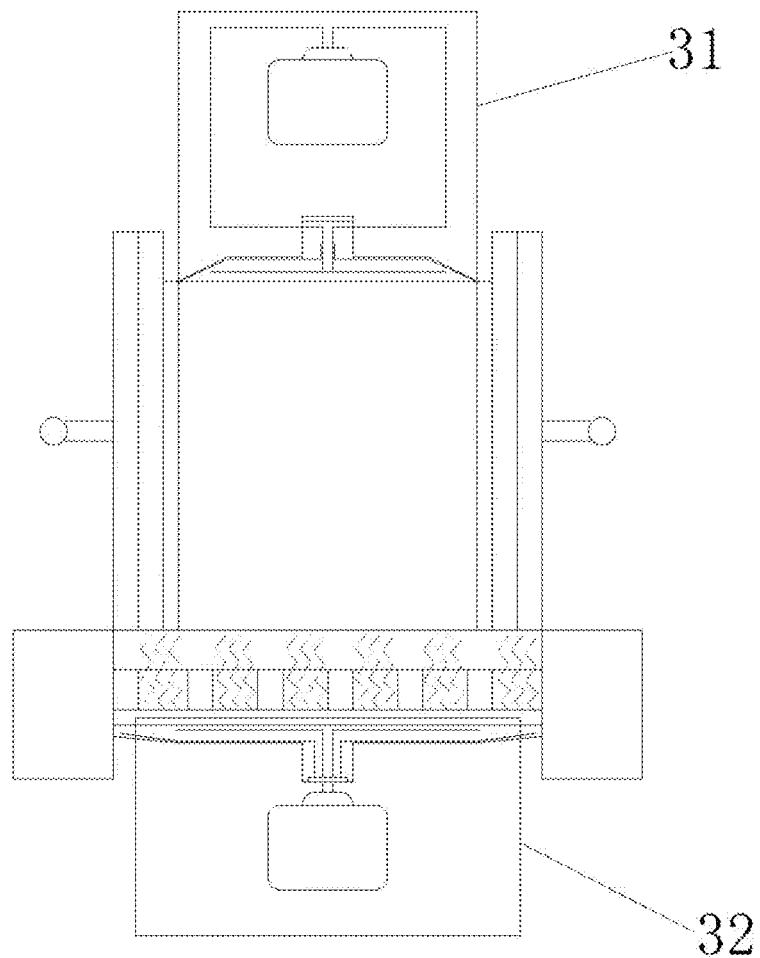
FIG. 6 is a schematic diagram of arrangement of the refrigeration, water and salt supplementation unit according to Embodiment 1 of the present disclosure.
Figure 7:
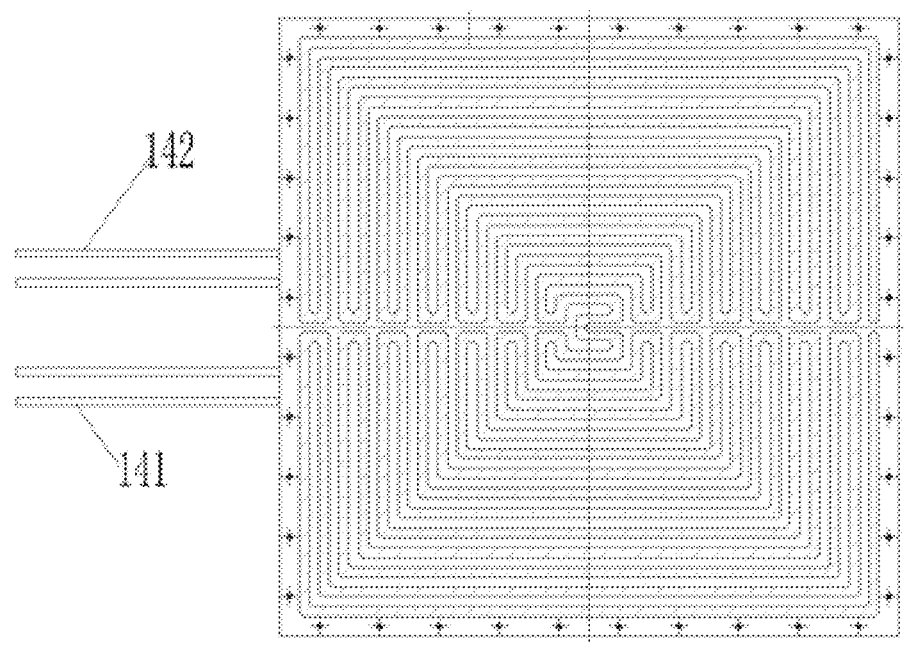
FIG. 7 is a schematic structural diagram of a water permeation plate according to Embodiment 1 of the present disclosure.

In an actual geological environment, freeze-thaw migration of salt in the soil is that salt is dissolved in water and is subjected to freeze-thaw migration along with the water. In order to simulate an actual freeze-thaw process, a soil unit is cooled, frozen, heated, and thawed from the upper end, and the soil unit is supplemented with water and salt as well as discharges water and salt from the lower end. Therefore, the lower end of the soil unit is provided with a water and salt supply and drainage system to supplement water and salt to or discharge water and salt from the soil unit. As shown in FIG. 6, the refrigeration, water and salt supplementation unit includes a refrigeration module 31 and a water and salt supplementation module 32. The refrigeration module includes a cooling pipe 141 arranged below a groove on the inner lower side of the normal loading plate 17 and the water permeation plate 14. By means of circulating normally loaded internal cooling liquid in the cooling pipe, a temperature load is applied to the top and the bottom of the soil test sample; the refrigeration equipment adjusts different cooling liquid temperatures to apply different freeze temperature loads and simulate a temperature gradient. The water and salt supplementation module conveys water or salt to the bottom plate 12 through a circulating pipe, and the water or salt is supplemented to the water supply and drainage trough through the water supply and drainage port of the bottom plate and is permeated to the water permeation plate through the water supply and drainage trough; and the water or salt is supplemented to the soil test sample under the capillary action. It should be noted that in this solution, the structural design of the water permeation plate 14 is that the upper and lower surfaces are provided with slots. As shown in FIG. 7, a water and salt pipe 142 is disposed above, and the cooling pipe 141 is disposed below.

Figure 8:
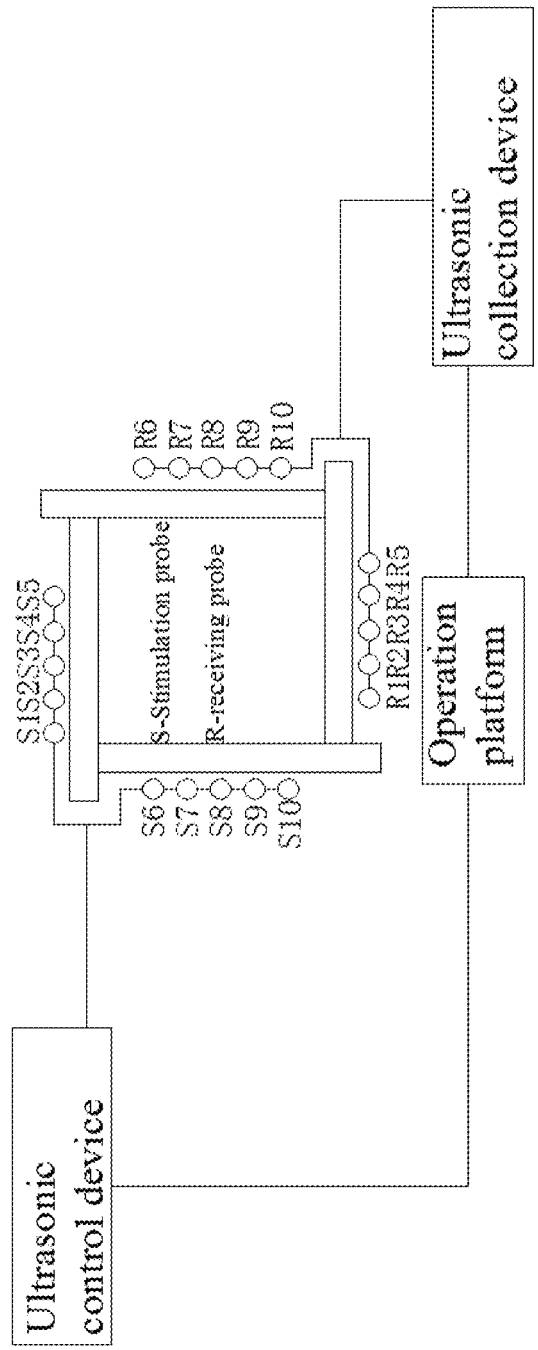
FIG. 8 is a schematic diagram of structural arrangement of a soil structure change monitoring unit according to Embodiment 1 of the present disclosure.

In the test, physical quantities that need to be tracked for dynamic monitoring and real-time displaying mainly include deformation characteristics and structural changes of the soil, and parameters such as total water content, unfrozen water content, ice content, salt migration and temperature changes. Specifically, the soil-water-ice-salt change monitoring unit includes a soil structure change monitoring module and a water-ice-salt change monitoring module. The soil structure change monitoring module mainly uses an ultrasonic device. Several ultrasonic stimulation probes and receiving probes are reasonably arranged outside the soil box. The two types of probes are arranged in one-to-one correspondence. As shown in FIG. 8, the ultrasonic device is arranged on the outer side of the soil box. The stimulation probes are installed on one side of the soil box, and the receiving probes are installed on the other side to collect received signals, so that changes in the soil structure in the testing process are reflected. The water-ice-salt change monitoring module includes sensors at different depths in the environmental soil region to monitor the water, ice, and salt contents of the soil test sample.

Figure 9:
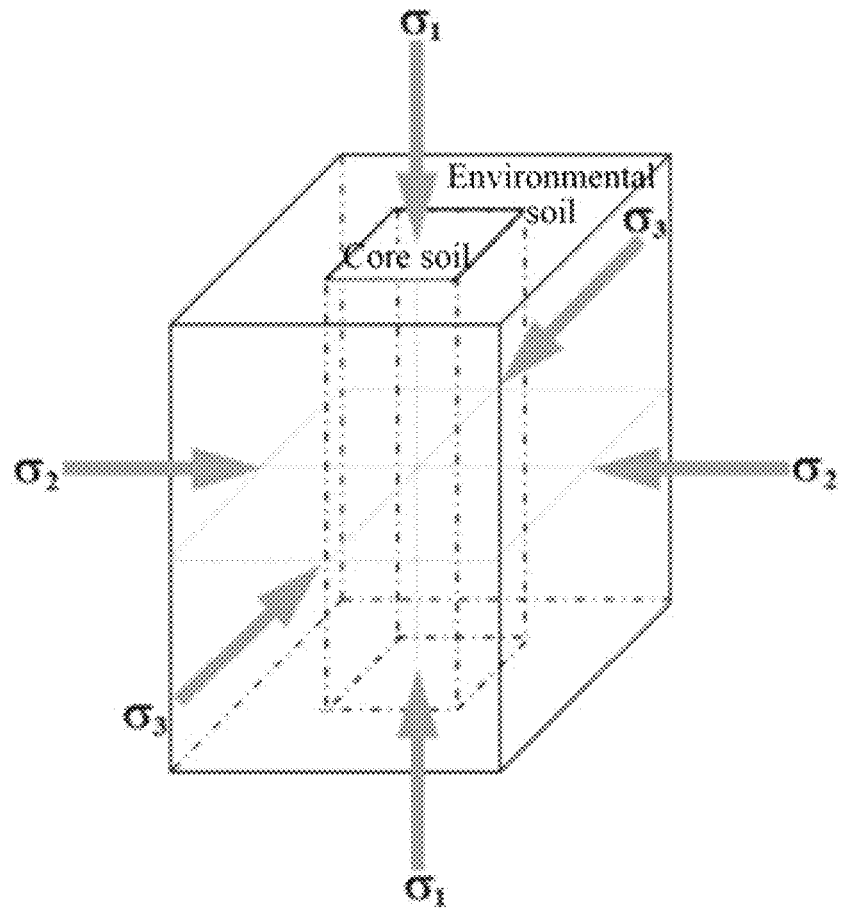
FIG. 9 is a schematic diagram of divided regions of soil test samples according to Embodiment 1 of the present disclosure.
Figure 10:
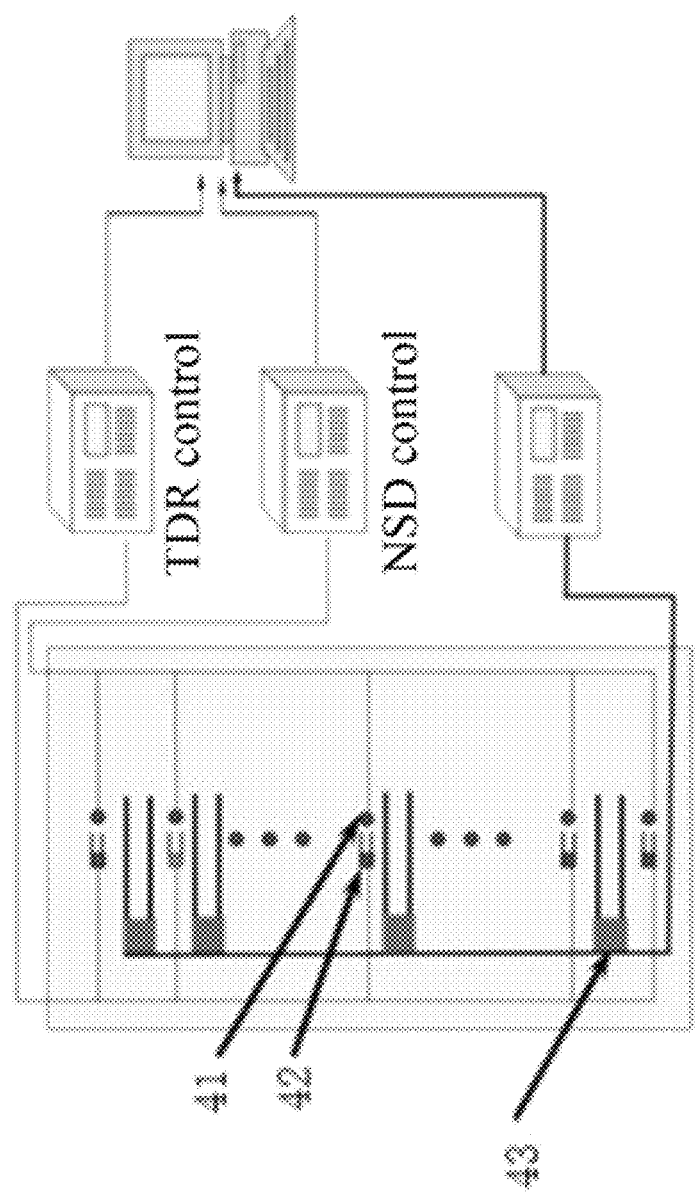
FIG. 10 is a schematic diagram of arrangement positions of monitoring sensors for water, ice, and salt contents in Embodiment 1 of the present disclosure.

Based on the concept of unit test, a loading mode that the three principal stresses are independently controlled is adopted. As shown in FIG. 9, the large-size soil test sample is divided into an environmental soil region (length 1.2 m×width 1.2 m×height 1.0 m except a core soil region) and the core soil region (length 1.0 m×width 1.0 m×height 1.0 m). The reasonability of the design scale of the soil is subjected to detailed numerical value simulation analysis in combination with finite element analysis to verify the reasonability and effectiveness. In order to realize distributed measurement of the water content of the whole cross-section of the soil (the environmental soil region and the core soil region), the monitoring sensors for the water, ice and salt contents are arranged in the environmental soil region at different depths. In the present embodiment, a plurality of neutron scatterometers are arranged at intervals vertically from top to bottom in the soil. The actual number of neutron scatterometers is specifically designed according to a radiation radius of neutrons, the size of the soil unit, and the requirement for detection accuracy. A TDR probe is arranged within the radiation radius of each neutron scatterometer. As shown in FIG. 10, element 41 represents an NSD probe, element 42 represents the TDR probe, and element 43 represents a salt sensor. The total water content in the soil test sample is monitored by using an NSD method, and the unfrozen water content in the soil test sample is monitored by a TDR method. The total ice content can be calculated from total ice content=total water content−unfrozen water content, which is convenient for realizing water and ice monitoring. For salt monitoring, the contents of the supplemented salt at different depths in the soil test sample is mainly tested, that is, a cation or anion content of the salt in the soil test sample is monitored, and the law of migration of salt in the soil test sample is obtained according to the law of migration of ions. In addition, traditional measurement of displacement, force and temperature is realized by the loading device and by arranging the corresponding sensors in the environmental soil region.

The soil is divided into the environmental soil region and the core soil region. The reasons and advantages of this design are as follows. (1) Since the core soil region is relatively large, and soil that simulates an environment where the core soil region is located is provided around, the scale effect of the core soil region can be reduced to the maximum extent. (2) The large-scale requirement that more different types of sensors are arranged in the environmental soil region without a significant impact on the performance of the core soil region is satisfied. (3) The soil property, the initial water content, the filling compactness, the filling height, etc. of the core soil region are completely consistent with those of the environmental soil, so the permeability, heat transfer, modulus, etc. of them can be kept consistent, thereby ensuring that consistent temperature migration, water migration and salt migration occurs between the core soil region and the environmental soil in the test, and the same migration gradient is achieved at the same height. (4) Since the loading mode that the three principal stresses are independently controlled, two actual three-dimensional stress states are well simulated. (5) Since the environmental soil with a certain thickness is disposed around the core soil body, an actual state of the core soil region in a site or a foundation is well simulated. The core soil region is an object emphatically inspected or concerned in a freeze-thaw test, so the friction effect on the boundary of a test piece (soil unit) due to the use of existing test equipment to carry out the freeze-thaw test is avoided.

Based on this design solution of the core soil region and the environmental soil region, in combination with the design of the soil box structure, the three-dimensional loading unit, etc., an actual system three-dimensional open and three-dimensional stress state of the engineering geological environment in cold regions can be well simulated, and experimental studies on the multi-field coupling, such as temperature, water, salt, stress and strain, and mutual feedback effect problems are scientifically and reasonably conducted.

Embodiment 2, the present embodiment makes the following introduction to an assembling method for the geotechnical true triaxial multi-field coupling test system based on the system disclosed in Embodiment 1.

At step 1: the base, the bottom plate, the water supply and drainage trough, and the water permeation plate are installed in sequence;

the bottom plate is placed on the base; the water supply and drainage trough is arranged on the upper surface of the bottom plate, and is mainly composed of steel vertical columns and a bottom plate with a slope; the water supply and drainage port is formed in the middle of the bottom plate; the water permeation plate is arranged on the upper surface of the water supply and drainage trough to ensure that water entering the water supply and drainage trough is uniformly supplemented to the soil test sample through the water permeation plate.

At step 2: the soil box side plates are installed; the assembling of the soil box is completed according to the soil box horizontal deformation limiting device; and the waterproof sealing strips are arranged between the soil box side plates as well as between the soil box side plates and the bottom plate.

In order to prevent heat exchange between the soil in the soil box and the external environment, the soil box side plates are composed of three plates: a thermal insulation plate is sandwiched between an outer side plate and the inner side plate. In order to prevent an excessive horizontal deformation of the soil box in the testing process, each side plate is provided with a soil box horizontal deformation limiting device, that is, the maximum stroke of the side plate depends on the maximum range of the limiting device.

At step 3: the soil box is filled with soil layer by layer, the sensors are arranged in the environmental soil region, and filling of soil test samples is completed.

For water-ice-salt change monitoring, the water, ice and salt contents of the soil test sample are monitored through the corresponding sensors arranged in the environmental soil region.

At step 4: ultrasonic monitoring equipment is arranged around the soil box side plates.

The soil structure change monitoring system is arranged on the outer side of the soil box; one side of the soil box is provided with the stimulation probes, and the other side is provided with the receiving probes; and the changes in the soil structure in the testing process are reflected by means of collecting received signals.

At step 5: the hollow square fender is provided; the normal loading plate is arranged in the hollow square fender; and the soil test sample is installed on a true triaxial test machine.

In order to make the normal loading plate to normally apply a normal load to the soil during movement of the soil box side plates, the hollow square fender needs to be placed at the top of the lateral loading plate; when the lateral loading plate moves, the hollow square fender is kept in close contact with the lateral loading plate; the soil in the soil box is applied with a load through the normal loading plate; and the maximum stroke of the normal loading plate is the thickness of the hollow square fender.

At step 6: the refrigeration equipment is connected to the cooling pipe in the normal loading plate through the circulating pipe to apply a temperature load to the top of the soil test sample; the water and salt supplementation module is arranged at the bottom of the bottom plate to apply water and salt to the bottom of the soil test sample.

In a refrigeration system, in order to simulate a freezing process of the actual soil (i.e., frozen from top to bottom), the cooling pipe is arranged in the normal loading plate, and the cooling liquid is circulated in the cooling pipe through the external refrigeration equipment; the temperature load is applied to the top of the soil test sample through the bottom of the normal loading plate; and different freezing temperatures at the top of the soil test sample are simulated by adjusting different cooling liquid temperatures. The water and salt supplementation system supplements water or salt into the water supply and drainage trough through the water supply and drainage port of the bottom plate by means of the circulation pipe, and the water or salt is permeated into the water permeation plate through the water supply and drainage trough and is transmitted into the soil test sample through the capillary action. In the water and salt supplementation system, water or salt volume measurement equipment is used to measure the volume of the water or salt supplemented into the soil test sample during the test. Therefore, the temperature load is applied to the top of the soil test sample and the water and salt are supplemented to the bottom, so that a system open state of the soil test sample in the testing process is well realized.

At step 7: the horizontal and normal loading modules are provided to load three stresses in different directions.

In the testing process, a level gauge is arranged on the dowel bar to ensure that coaxial loading can be realized in two horizontal directions. A horizontal dynamic load is provided by a horizontal hydraulic oil cylinder and the horizontal power loading fine adjustment device; the normal power loading device applies a normal load to the normal loading plate; the hollow square fender loading device ensures that the hollow square fender and the side plates are kept in close contact in the testing process; and the system vertical columns and the cross beam ensure that normal loading is realized.

This solution is based on the deformable large-size soil box structure, and the thermal insulation plate is sandwiched between the inner and outer side plates of soil box side plates, so that the heat exchange between the soil in the soil box and the external environment can be effectively avoided. In combination with the soil box horizontal deformation limiting device, it is ensured that the soil box in the testing process will not have excessive horizontal deformation. In the horizontal power loading structure, the level gauge is arranged on the dowel bar, it can be ensured that coaxial loading can be realized in two horizontal directions. In the design of the refrigeration, water and salt supplementation unit, the temperature load is applied to the soil test sample through the normal loading plate at the top, and the water and salt are supplemented to the soil test sample through the bottom plate at the bottom, so that the freezing and water and salt supplementing processes of the actual soil can be fully simulated, and the system open state of the soil test sample in the testing process is realized. In the design of the soil-water-ice-salt change monitoring unit, conventional true triaxial soil samples are relatively small, and too many sensors are provided, resulting in that the monitoring instruments affect the characteristics of the soil samples. This solution proposes that the monitoring sensors are arranged on the outer side of the soil box or in the environmental soil region, so that the influence of the monitoring instruments on the internal structure of the soil test samples is solved, and a multi-field coupling test, rather than a spot test, for the soil is well realized.

Only preferred embodiments of the present disclosure are described above, and are not intended to limit the present disclosure in other forms. Anyone skilled in the art can change or modify the technical content disclosed above into equivalently changed equivalent embodiments which are applied to other fields. However, any simple alterations, equivalent changes and modifications made to the above embodiments according to the technical essence of the present disclosure without departing from the content of the technical solutions of the present disclosure still fall within the protection scope of the technical solutions of the present disclosure.

What is claimed is:

1. A temperature-controllable large-size geotechnical true triaxial multi-field coupling test system, comprising:
    a host loading mechanism;
    a deformable large-size soil box;
    an independent three-dimensional loading unit;
    a refrigeration, water and salt supplementation unit; and
    a soil-water-ice-salt change monitoring unit, wherein the deformable large-size soil box is arranged on the host loading mechanism; wherein the independent three-dimensional loading unit, the refrigeration, water and salt supplementation unit, and the soil-water-ice-salt change monitoring unit are all connected with the deformable large-size soil box to respectively correspondingly apply stress to the deformable large-size soil box, supplement refrigeration as well as water and salt, and monitor soil-water-ice-salt changes;
    wherein the host loading mechanism comprises a carrier base, a vertical loading framework, and a horizontal loading framework; the carrier base comprises a carrier table located below the vertical loading framework and a rail seat extending in a horizontal direction of the carrier table; the horizontal loading framework comprises a workbench, a lateral reaction frame, and a moving lifting wheel disposed below the workbench; the lateral reaction frame is disposed on the workbench through a lateral pressure vertical column; and the deformable large-size soil box is disposed on the workbench and is surrounded by the lateral reaction frame;
    wherein the deformable large-size soil box comprises a bottom plate, soil box side plates, a soil box horizontal deformation limiting device and a normal loading plate; a water supply and drainage trough is arranged on an upper surface of the bottom plate; a water permeation plate is arranged on the water supply and drainage trough; a lateral sliding device is also arranged on an outer side of each of the soil box side plates; a lateral oil cylinder is fixedly provided on the lateral reaction frame; the lateral oil cylinder passes through the lateral reaction frame and is connected with the lateral sliding device; and the lateral oil cylinder slides along the lateral sliding device in a deformation process of the deformable large-size soil box.

2. The temperature-controllable large-size geotechnical true triaxial multi-field coupling test system according to claim 1, wherein the refrigeration, water and salt supplementation unit comprises a refrigeration module and a water and salt supplementation module; the refrigeration module comprises a cooling pipe arranged below a groove on an inner lower side of the normal loading plate and the water permeation plate, and a refrigeration equipment connected with the cooling pipe; the water and salt supplementation module is connected with the water supply and drainage trough on the bottom plate through a circulating pipe, and is used to convey water or salt to the bottom plate through a circulating plate; and the water or salt is permeated from the water supply and drainage trough to the water permeation plate to supplement water or salt to soil under a capillary action.

3. The temperature-controllable large-size geotechnical true triaxial multi-field coupling test system according to claim 2, wherein grooves are formed in upper and lower surfaces of the water permeation plate; a water-salt pipe is arranged in an upper groove of the grooves of the water permeation plate, and the cooling pipe is arranged in a lower groove of the grooves of the water permeation plate.

4. The temperature-controllable large-size geotechnical true triaxial multi-field coupling test system according to claim 1, wherein the soil-water-ice-salt change monitoring unit comprises a soil structure change monitoring module and a water-ice-salt change monitoring module; the soil structure change monitoring module comprises an ultrasonic device, an ultrasonic stimulation probe and a receiving probe; the ultrasonic stimulation probe and the receiving probe are correspondingly arranged on an outer side of the deformable large-size soil box respectively; the water-ice-salt change monitoring module comprises monitoring sensors arranged at different depths in an environmental soil region to monitor water, ice, and salt contents of soil.

5. The temperature-controllable large-size geotechnical true triaxial multi-field coupling test system according to claim 3, wherein the soil in the deformable large-size soil box is divided into a core soil region and the environmental soil region surrounding the core soil region; the monitoring sensors comprise a plurality of neutron scatterometers arranged vertically in the environmental soil region at intervals from top to bottom; and a TDR probe is arranged within a radiation radius of each of the plurality of neutron scatterometers.

6. The temperature-controllable large-size geotechnical true triaxial multi-field coupling test system according to claim 4, wherein the core soil region is of a core column structure with length 1.0 m×width 1.0 m×height 1.0 m; and the environmental soil region is of a ring column structure obtained by removing the core soil region from a cubic structure with length 1.2 m×width 1.2 m×height 1.0 m.

7. The temperature-controllable large-size geotechnical true triaxial multi-field coupling test system according to claim 1, wherein the independent three-dimensional loading unit comprises a horizontal power loading module and a normal power loading module; the horizontal power loading module comprises a horizontal dowel bar, a level gauge, and a horizontal power loading fine adjustment device; the level gauge is arranged on the horizontal dowel bar; the normal power loading module comprises a normal power loading device, a hollow square fender, and a cross beam; an axial force is applied to the normal loading plate; and the normal loading plate is configured to downwards transmit load to soil in the deformable large-size soil box.

8. The temperature-controllable large-size geotechnical true triaxial multi-field coupling test system according to claim 1, wherein a push-pull arm is also arranged between the carrier table and the workbench; one end of the push-pull arm is fixedly connected with the workbench, and another end of the push-pull arm is mounted on the carrier table through a push-pull oil cylinder; and the workbench slides along the rail seat under an action of the push-pull oil cylinder.

9. The temperature-controllable large-size geotechnical true triaxial multi-field coupling test system according to claim 1, wherein each of the soil box side plates of the deformable large-size soil box comprises, from outside to inside in sequence, an outer side plate, a thermal insulation plate, and an inner side plate.

10. A test method based on a temperature-controllable large-size geotechnique true triaxial multi-field coupling test system that comprises:
   a host loading mechanism;
   a deformable large-size soil box;
   an independent three-dimensional loading unit;
   a refrigeration, water and salt supplementation unit; and
   a soil-water-ice-salt change monitoring unit;
   the deformable large-size soil box being arranged on the host loading mechanism; the independent three-dimensional loading unit, the refrigeration, water and salt supplementation unit, and the soil-water-ice-salt change monitoring unit being all connected with the deformable large-size soil box to respectively correspondingly apply stress to the deformable large-size soil box, supplement refrigeration as well as water and salt, and monitor soil-water-ice-salt changes;
   the host loading mechanism comprising a carrier base, a vertical loading framework, and a horizontal loading framework; the carrier base comprising a carrier table located below the vertical loading framework and a rail seat extending in a horizontal direction of the carrier table; the horizontal loading framework comprising a workbench, a lateral reaction frame, and a moving lifting wheel being disposed below the workbench; the lateral reaction frame being disposed on the workbench through a lateral pressure vertical column; and the deformable large-size soil box being disposed on the workbench and being surrounded by the lateral reaction frame;
   the deformable large-size soil box comprising a bottom plate, soil box side plates, a soil box horizontal deformation limiting device and a normal loading plate; a water supply and drainage trough being arranged on an upper surface of the bottom plate; a water permeation plate being arranged on the water supply and drainage trough; a lateral sliding device being also arranged on an outer side of each of the soil box side plates; a lateral oil cylinder being fixedly provided on the lateral reaction frame; the lateral oil cylinder passing through the lateral reaction frame and being connected with the lateral sliding device; and the lateral oil cylinder sliding along the lateral sliding device in a deformation process of the deformable large-size soil box;
   the test method comprising:
   pulling out the workbench, and assembling the deformable large-size soil box;
   filling the deformable large-size soil box with soil layer by layer, arranging monitoring sensors included in a water-ice-salt change monitoring module of soil-water-ice-salt change monitoring unit in an environmental soil region of the soil, completing filling of soil test samples, and arranging the water-ice-salt change monitoring module and a soil structure change monitoring module included in the soil-water-ice-salt change monitoring unit;
   resetting the workbench to the carrier table, arranging a hollow square fender included in a normal power loading module of the independent three-dimensional loading unit, and arranging the normal loading plate in the hollow square fender;
   connecting the refrigeration, water and salt supplementation unit, connecting a refrigeration equipment included in the refrigeration, water and salt supplementation unit to a cooling pipe included in a refrigeration module of the refrigeration, water and salt supplementation unit in the normal loading plate through a circulating pipe to realize apply a temperature load to a top of the soil test sample, and arranging a water and salt supplementation module included in the refrigeration, water and salt supplementation unit at a bottom of the bottom plate to apply water and salt to a bottom of the soil; and
   arranging a horizontal power loading module included in the independent three-dimensional loading unit and the normal power loading module to load three stresses in unequal directions.

* * * * *